US011135587B2

(12) United States Patent
Kojima et al.

(10) Patent No.: US 11,135,587 B2
(45) Date of Patent: Oct. 5, 2021

(54) PARTICLE TRAPPING CHIP, PARTICLE TRAPPING DEVICE, AND PARTICLE TRAPPING METHOD

(71) Applicant: SONY CORPORATION, Tokyo (JP)

(72) Inventors: Kensuke Kojima, Kanagawa (JP); Shin Masuhara, Tokyo (JP)

(73) Assignee: SONY CORPORATION, Tokyo (JP)

( * ) Notice: Subject to any disclaimer, the term of this patent is extended or adjusted under 35 U.S.C. 154(b) by 205 days.

(21) Appl. No.: 16/481,717

(22) PCT Filed: Nov. 21, 2017

(86) PCT No.: PCT/JP2017/041774
§ 371 (c)(1),
(2) Date: Jul. 29, 2019

(87) PCT Pub. No.: WO2018/154886
PCT Pub. Date: Aug. 30, 2018

(65) Prior Publication Data
US 2020/0023365 A1      Jan. 23, 2020

(30) Foreign Application Priority Data

Feb. 21, 2017   (JP) .............................. JP2017-029818

(51) Int. Cl.
*B01L 3/00*   (2006.01)
*C12M 3/06*   (2006.01)
*G01N 15/14*  (2006.01)

(52) U.S. Cl.
CPC ....... *B01L 3/502761* (2013.01); *C12M 23/16* (2013.01); *G01N 15/1404* (2013.01);
(Continued)

(58) Field of Classification Search
CPC ..... B01L 2200/0636; B01L 2200/0668; B01L 3/502761; B81B 1/00; C12M 23/16;
(Continued)

(56) References Cited

U.S. PATENT DOCUMENTS

2013/0078163 A1*  3/2013  Chung .................. C12M 21/06
                                                               422/502
2017/0007996 A1*  1/2017  Azpiroz ............ B01L 3/502761

FOREIGN PATENT DOCUMENTS

JP    2009-125635 A    6/2009
JP    2011-000079 A    1/2011
(Continued)

OTHER PUBLICATIONS

International Search Report and Written Opinion of PCT Application No. PCT/JP2017/041774, dated Feb. 20, 2018, 10 pages of ISRWO.

(Continued)

*Primary Examiner* — Jennifer Wecker
(74) *Attorney, Agent, or Firm* — Chip Law Group

(57) ABSTRACT

There is provided a particle supplementing chip provided with a structure for trapping a particle, and for preventing the trapped particle from being greatly deformed by a suction force. With respect to this point, the present technology provides a particle trapping chip including a first channel, a second channel, a first recess that is open on the first channel side, a second recess that is provided side by side with the first recess, a connecting portion connecting the first recess and the second recess, and a communicating portion allowing the second recess and the second channel to communicate with each other.

20 Claims, 8 Drawing Sheets

(52) U.S. Cl.
CPC ............ *B01L 2200/0636* (2013.01); *B01L 2200/0668* (2013.01)

(58) Field of Classification Search
CPC ...... C12M 23/34; C12M 33/04; C12M 45/02; C12M 47/04; G01N 15/1404; G01N 37/00
See application file for complete search history.

(56) References Cited

FOREIGN PATENT DOCUMENTS

| | | |
|---|---|---|
| JP | 2012-075391 A | 4/2012 |
| WO | 2010/147078 A1 | 12/2010 |

OTHER PUBLICATIONS

Tan, et al., "Dynamic Microarray System with Gentle Retrieval Mechanism for Cell-Encapsulating Hydrogel Beads", The Royal Society of Chemistry, Lab Chip vol. 8, Dec. 18, 2007, pp. 259-266.

Zhou, et al., "A Microfluidic Platform for Trapping, Releasing and Super-Resolution Imaging of Single Cells", Sensors and Actuators B vol. 232, Mar. 25, 2016, pp. 680-691.

McDonald, et al., "Poly(dimethylsiloxane) as a Material for Fabricating Microfluidic Devices", Accounts of Chemical Research, vol. 35, No. 7, Jul. 2002, pp. 491-499.

Tan, et al., "Dynamic microarray system with gentle retrieval mechanism for cell-encapsulating hydrogel beads", The Royal Society of Chemistry, Lab Chip, vol. 8, No. 2, Feb. 2008, pp. 259-266.

Zhou, et al., "A microfluidic platform for trapping, releasing and super-resolution imaging of single cells", Sensors and Actuators B: Chemical, vol. 232, Sep. 2016, pp. 680-691.

Tan, et al., "Dynamic Microarray System with Gentle Retrieval Mechanism for Cell-Encapsulating Hydrogel Beads", The Royal Society of Chemistry, Lab Chip, vol. 8, No. 2, Nov. 29, 2007, pp. 259-266.

Zhou, et al., "A Microfluidic Platform for Trapping, Releasing and Super-Resolution Imaging of Single Cells", Sensors and Actuators B: Chemical, vol. 232, Mar. 25, 2016, pp. 680-691.

\* cited by examiner

FIG. 9
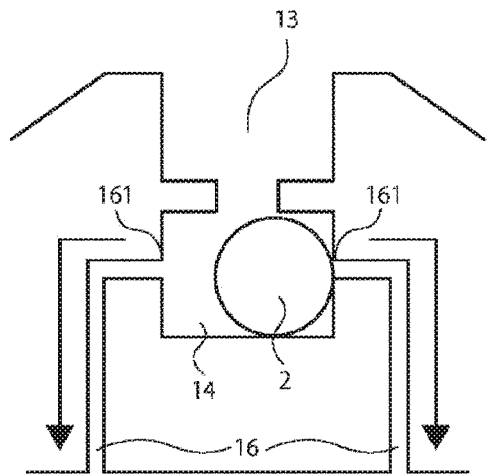
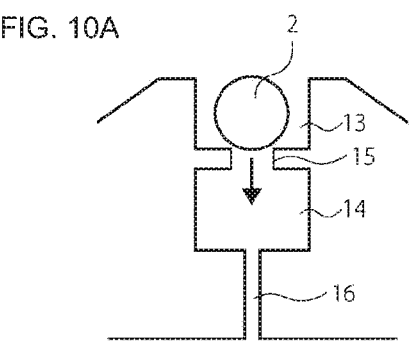
FIG. 10A
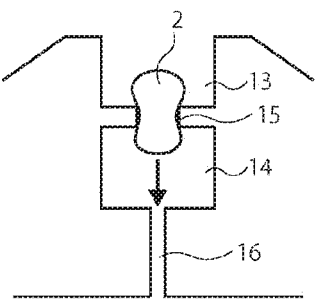
FIG. 10B
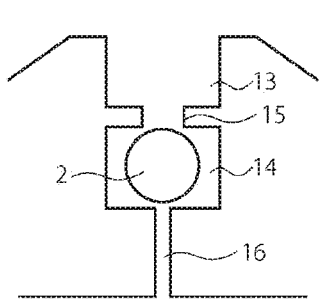
FIG. 10C
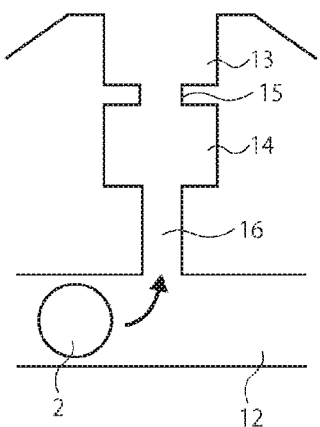
FIG. 11A
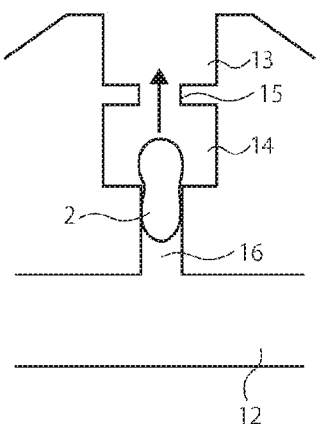
FIG. 11B
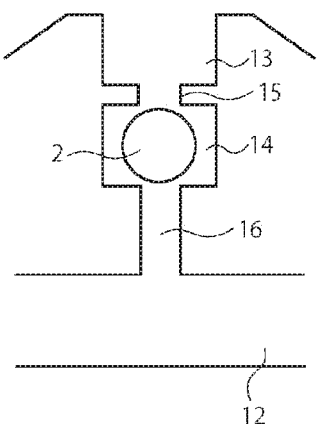
FIG. 11C

PARTICLE TRAPPING CHIP, PARTICLE TRAPPING DEVICE, AND PARTICLE TRAPPING METHOD

CROSS REFERENCE TO RELATED APPLICATIONS

This application is a U.S. National Phase of International Patent Application No. PCT/JP2017/041774 filed on Nov. 21, 2017, which claims priority benefit of Japanese Patent Application No. JP 2017-029818 filed in the Japan Patent Office on Feb. 21, 2017. Each of the above-referenced applications is hereby incorporated herein by reference in its entirety.

TECHNICAL FIELD

The present technology relates to a particle trapping chip, a particle trapping device, and a particle trapping method.

BACKGROUND ART

In recent years, technologies for trapping a cell, represented by flow cytometry and the like, are being developed. A cell is provided for analysis or culture after being trapped.

For example, as a method for trapping a cell, a technology described in Patent Document 1 was developed. Patent Document 1 discloses a structure according to which a well having a size allowing a cell to enter is carved on a channel where a cell-containing sample flows, and a slit is provided in the well so as to allow suction of a cell (FIG. 23, FIG. 25, etc.)

CITATION LIST

Patent Document

Patent Document 1: US 2013/0078163 A

SUMMARY OF THE INVENTION

Problems to be Solved by the Invention

However, with the channel structure of Patent Document 1 described above, there are cases where it is difficult to appropriately maintain a cell inside the well, due to a captured cell being greatly deformed by a suction force through the slit, and the cell receiving great stress or being drawn into the slit as a result. On the other hand, if the suction force is reduced, there are cases where the cell does not reach a wall surface where the well is arranged, or where the cell is not sucked into the well even if the wall surface is reached.

Accordingly, the present technology has its main object to provide a particle supplementing chip provided with a structure for trapping a particle, and for preventing the trapped particle from being greatly deformed by a suction force.

That is, the present technology provides a particle trapping chip including a first channel; a second channel; a first recess that is open on the first channel side; a second recess that is provided side by side with the first recess; a connecting portion connecting the first recess and the second recess; and a communicating portion allowing the second recess and the second channel to communicate with each other.

The particle trapping chip may further include a plug member that is housed in the second recess.

The plug member may include a bead.

A binding substance that binds to a target substance may be immobilized on a surface of the plug member.

The connecting portion may include an elastic member.

A joining portion between the second recess and the communicating portion may be provided below the second recess.

A joining portion between the second recess and the communicating portion may be provided on a side of the second recess.

A lower surface of the first channel may include a corrugated structure including a ridge portion and a trough portion, and the first recess may be provided at a crest portion of the ridge portion.

Furthermore, the present technology provides a particle trapping device including a particle supplementing chip including a first channel, a second channel, a first recess that is open on the first channel side, a second recess that is provided side by side with the first recess, a connecting portion connecting the first recess and the second recess, and a communicating portion allowing the second recess and the second channel to communicate with each other; and a liquid feed unit.

The particle trapping device may further include a waste liquid unit.

The particle trapping device may further include an observation unit configured to observe the first recess.

The particle trapping device may further include a liquid feed control unit configured to control the liquid feed unit.

Furthermore, the present technology provides a particle trapping method performed using a particle supplementing chip including a first channel, a second channel, a first recess that is open on the first channel side, a second recess that is provided side by side with the first recess, a connecting portion connecting the first recess and the second recess, and a communicating portion allowing the second recess and the second channel to communicate with each other, the method including feeding a sample containing a plug member to the first channel, trapping the plug member in the first recess, moving the trapped plug member to the second recess by suction through the communicating portion, feeding a sample containing a particle to the first channel, and trapping the particle in the first recess.

Furthermore, the present technology provides a particle trapping method performed using a particle supplementing chip including a first channel, a second channel, a first recess that is open on the first channel side, a second recess that is provided side by side with the first recess, a connecting portion connecting the first recess and the second recess, a communicating portion allowing the second recess and the second channel to communicate with each other, and a plug member that is housed in the second recess, the method including feeding a sample containing a particle to the first channel, and trapping the particle in the first recess.

The particle trapping method may further include causing the feeding to be performed backward.

Furthermore, the present technology provides an acquisition method of a target substance performed using a particle supplementing chip including a first channel, a second channel, a first recess that is open on the first channel side, a second recess that is provided side by side with the first recess, a connecting portion connecting the first recess and the second recess, and a communicating portion allowing the second recess and the second channel to communicate with each other, the method including: a step of feeding, to the first channel, a sample containing a plug member on which a binding substance that binds to the target substance is immobilized, trapping the plug member in the first recess, moving the trapped plug member to the second recess by suction through the communicating portion, feeding a sample containing a particle to the first channel, and trapping the particle in the first recess; a step of causing the target substance derived from the particle and the binding substance to react with each other; and a step of removing the plug member from the second recess.

Furthermore, the present technology provides an acquisition method of a target substance performed using a particle supplementing chip including a first channel, a second channel, a first recess that is open on the first channel side, a second recess that is provided side by side with the first recess, a connecting portion connecting the first recess and the second recess, a communicating portion allowing the second recess and the second channel to communicate with each other, and a plug member that is housed in the second recess, and on which a binding substance that binds to the target substance is immobilized, the method including: a step of feeding a sample containing a particle to the first channel, and trapping the particle in the first recess; a step of causing the target substance derived from the particle and the binding substance to react with each other; and a step of removing the plug member from the second recess.

In the acquisition method of a target substance, the plug member may be removed from the second recess by using a capillary.

In the acquisition method of a target substance, the plug member may be caused to flow out of the second recess into the first channel by generating a liquid flow in an opposite direction from the suction, a plug member-containing liquid may be collected from the first channel, and the plug member may be removed from the plug member-containing liquid.

Effects of the Invention

According to the present technology, there may be provided a particle trapping chip provided with a structure for trapping a particle, and for preventing the trapped particle from being greatly deformed by a suction force. Additionally, the effects of the present technology are not limited to the effects described above, and may be any of the effects described in the present specification.

BRIEF DESCRIPTION OF DRAWINGS

FIG. 9 is a schematic view showing an example of a communicating portion.

FIGS. 10A, 10B, and 10C are diagrams showing an example of a procedure of housing a plug member in a second recess.

FIGS. 11A, 11B, and 11C are diagrams showing an example of a procedure of housing the plug member in the second recess.

MODE FOR CARRYING OUT THE INVENTION

Hereinafter, a preferred mode for carrying out the present technology will be described with reference to the drawings. Additionally, the embodiment described below is a representative embodiment of the present technology, and shall not be construed to limit the scope of the present technology. The description will be given in the following order.
 1. Particle Trapping Chip
 2. Particle Trapping Device
 3. Particle Trapping Method
 4. Acquisition Method of Target Substance
1. Particle Trapping Chip The type of particles that are taken as targets of trapping by a particle trapping chip of the present technology are not particularly limited. For example, there may be cited bio-related particles such as cells, microorganisms and liposomes, synthetic particles such as latex particles, gel particles and industrial particles, or microbumps as terminals of connection portions of semiconductor chips or semiconductors, bead solar cells, and the like. Furthermore, sizes, shapes and the like of the particles are not particularly limited.

Figure 1:
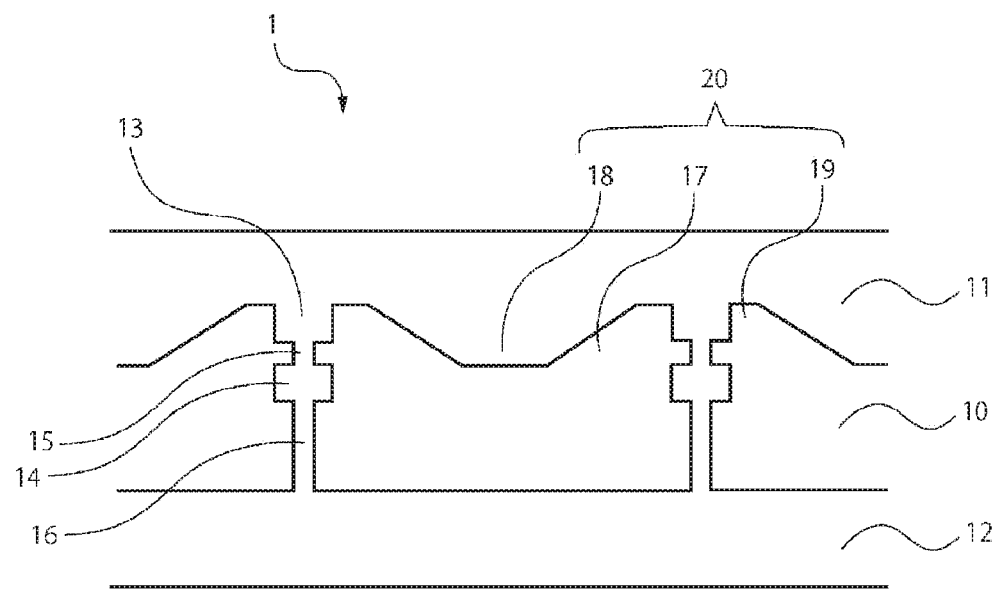
FIG. 1 is a transverse cross-sectional view of a particle trapping chip.
Figure 2:
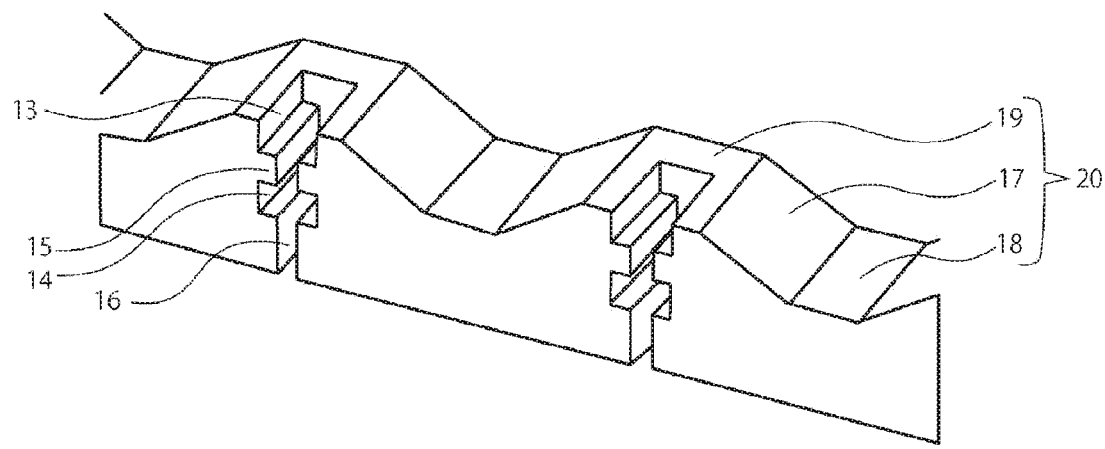
FIG. 2 is a perspective view of the particle trapping chip.

Next, a structure of a particle trapping chip 1 of the present technology will be described with reference to FIGS. 1 and 2. FIG. 1 is a transverse cross-sectional view of the particle trapping chip 1, and FIG. 2 is a perspective view of the particle trapping chip 1. The particle trapping chip 1 includes a first channel 11 on a substrate 10. The first channel 11 is formed on an upper surface side of the substrate 10. A sample flows through the first channel 11.

A material of the substrate 10 is not particularly limited, and resins such as polyethylene, polypropylene, polyvinyl chloride resin, polystyrene, polyethylene terephthalate, acrylic resin, polycarbonate, fluororesin, polybutyleneterephthalate, phenol resin, melamine resin, epoxy resin, unsaturated polyester resin, and dimethylpolysiloxane, glass, metal, and the like may be cited, for example.

The particle trapping chip 1 of the present technology includes a first recess 13 that is open on the first channel 11 side, a second recess 14 that is provided side by side with the first recess 13, and a connecting portion 15 connecting the first recess 13 and the second recess 14.

The first recess 13 is formed on a lower surface of the first channel 11. A particle that is contained in a sample flowing through the first channel 11 may be trapped in the first recess 13. The second recess 14 is provided on a lower surface side of the first recess 13, and is connected with the first recess 13 via the connecting portion 15.

The particle trapping chip 1 also includes a second channel 12, and a communicating portion 16 allowing the second recess 14 and the second channel 12 to communicate with each other. The second channel 12 is formed on a lower surface side of the substrate 10. A plug member may be housed in the second recess 14 (details will be given later).

Figure 3:
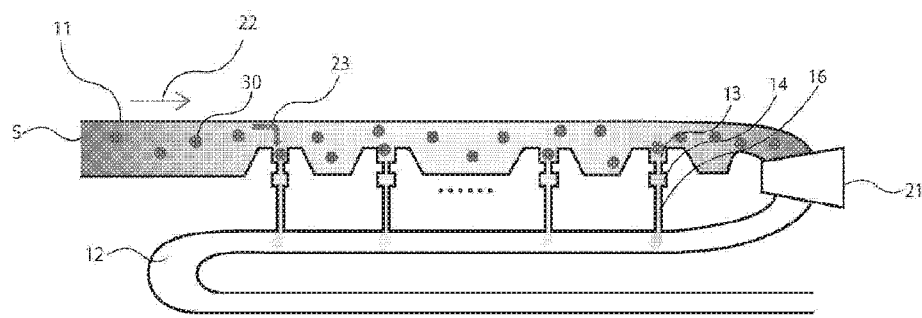
FIG. 3 is a schematic view showing an example of trapping of particles by the particle trapping chip.

Next, before further describing the configuration, a flow of particles in the particle trapping chip 1 will be described with reference to FIG. 3. FIG. 3 is a schematic view showing an example of trapping of particles by the particle trapping chip 1. In the example shown in FIG. 3, the first channel 11 and the second channel 12 are connected, and a valve 21 is provided at a connection part. A sample S containing particles 30 flows in a flow direction 22 of a liquid, and flows further downstream when the valve 21 is opened. Then, a suction force 23 due to a positive pressure is generated in a direction from the first channel 11 to the second channel 12, through the first recess 13, which is open on the first channel 11 side, the second recess 14 connected with the first recess 13, and the communicating portion 16 allowing the second recess 14 and the second channel 12 to communicate with each other. The particle 30 is sucked toward the first recess 13 by the suction force 23, and is trapped inside the first recess 13.

Additionally, the valve is not limited to be installed in the above manner. For example, a valve for causing a sample to flow may be installed on an upstream of the first channel 11, and a valve for sucking in the sample may be installed on a downstream of the second channel 12.

Referring back to FIGS. 1 and 2, a description will be further given of the first channel 11. In a case where the particle trapping chip 1 aims to trap a single particle, a corrugated structure 20 including ridge portions 17 and trough portions 18 is desirably provided on a lower surface of the first channel 11, and the first recess 13 is desirably formed at a crest portion 19 of the ridge portion 17. Because the corrugated structure 20 is provided, other particles are less likely to adhere to a particle that is trapped in the first recess 13 located at the crest portion 19, and accumulation of particles may be prevented. A state where two or more particles are trapped in one first recess 13 may thereby be avoided.

Figure 4:
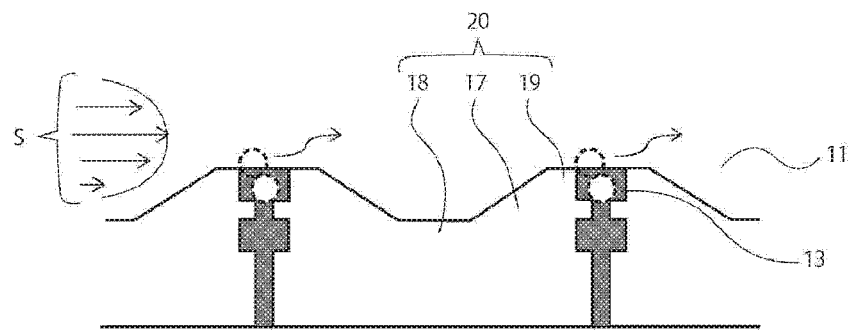
FIG. 4 is a schematic view showing an example of trapping of a particle in a first channel.

Next, a flow of particles in the first channel 11 will be described with reference to FIG. 4. FIG. 4 is a schematic view showing an example of trapping of a particle in the first channel 11. As shown in FIG. 4, a liquid flow of the sample S is a laminar flow in the first channel 11, and is characteristic in that a flow velocity is constantly higher at a center of the first channel 11 than near a side surface of the channel. Accordingly, by providing the first recess 13 at the crest portion 19 of the corrugated structure 20, occurrence of doublet according to which two or more particles enter the first recess 13 may be prevented (broken-line circles). That is, it is assumed that, because the flow velocity is high, even if a second particle is attached to cause doublet, second and later particles are carried away by the central laminar flow and do not easily enter inside. For example, the central laminar flow is about 20% faster compared to the flow velocity of the entire liquid flow.

Referring back to FIGS. 1 and 2, the configuration of the particle trapping chip 1 will be further described.

Widths and heights of the first channel 11 and the second channel 12 are not particularly limited, and may be determined according to a size, a shape and a type of a particle that is a target of trapping, or an amount or viscosity of a sample that flows through the channel, or the like.

Shapes of the first recess 13 and the second recess 14 are not particularly limited, and a circular shape, a truncated cone shape, an inverted truncated cone shape, an elliptical columnar shape, a truncated elliptical shape, an inverted truncated elliptical shape, a tapered shape, an inverted tapered shape, or a polygonal columnar shape with three or more sides may be cited, for example.

A depth of the first recess 13 is desirably equal to or smaller than a particle diameter of a particle that is to be trapped. Such a depth may prevent doublet of particles in the first recess 13 or accumulation of other particles on a trapped particle.

The "particle diameter" here of a particle refers to an average value of a major axis diameter and a minor axis diameter of the particle. Specifically, in a case of fine particles, the particle diameter may be calculated by measuring a substantial number (such as a hundred) of arbitrary fine particles using a microscope and by image processing software or the like, and by determining a number average.

For example, the depth of the first recess 13 is desirably two or less, or more desirably, one or less, in terms of ratio to the particle diameter of the particle that is to be trapped. Alternatively, the depth of the first recess 13 is desirably two or less, or more desirably, one or less, in terms of ratio to a diameter of an inscribed circle at an opening of the first recess 13. Furthermore, in a case where the first channel 11 includes the corrugated structure 20 including the ridge portion 17 and the trough portion 18, the depth of the first recess 13 may desirably be one or less, or more desirably, 0.8 or less, in terms of ratio of a height from the trough portion 18 to the ridge portion 17.

Furthermore, in a case where the first recess 13 has a three-dimensional shape with a circular opening, such as a columnar shape, a truncated cone shape, an inverted truncated cone shape, a tapered shape, or an inverted tapered shape, for example, a diameter of the first recess 13 is desirably a size that is at least one time and less than two times the particle diameter of the particle that is to be trapped. Moreover, in a case where the opening of the first recess 13 is a polygon with three or more sides, a perpendicular line from an apex angle to a base may be taken as the diameter in a case of an n-polygon where n is an odd number, and a diagonal line may be taken as the diameter in a case of an n-polygon where n is an even number. If the diameter is less than one time, a single cell cannot easily enter the first recess 13, and if the diameter is two or more times, a plurality of cells possibly enters the first recess 13.

In a case where the first channel 11 includes the corrugated structure 20 including the ridge portion 17 and the trough portion 18, the height from the trough portion 18 to the ridge portion 17 is desirably equal to or greater than the particle diameter of the particle that is to be trapped. The flow velocity of the sample inside the first channel 11 becomes faster, the closer to a center. Accordingly, in a case where the height of the ridge portion 17 and the trough portion 18 is smaller than the particle diameter of the particle, the flow velocity received by the particle is reduced also near the ridge portion 17. If the flow velocity near the ridge portion 17 is low, a particle following a particle that is trapped in the first recess 13 is more likely to adhere to the trapped particle. If the flow velocity is low, following particles collide with small energy and thus adhere to the trapped particle, thereby causing accumulation of particles.

A pitch between the ridge portions 17 may be made a length that is two or more times and 20 or less times the particle diameter of the particle that is to be trapped. Specifically, a length from the crest portion 19 of the ridge portion 17 to the crest portion 19 of the ridge portion 17 that is adjacent across one trough portion 18 is two or more times and 20 or less times the particle diameter of the particle that is to be trapped. If the length is less than two times, the particle possibly enters the trough portion 18, and if the length exceeds 20 times, the corrugated structure 20 possibly becomes close to a flat structure, depending on the height of the ridge portion 17, and the effects of the present technology are possibly not sufficiently achieved.

Additionally, the pitch between the ridge portions 17 is more desirably a length that is five or more times and 15 or less times the particle diameter of the particle that is to be trapped. In such a range, the effects achieved by the corrugated structure 20 of the present technology are enhanced. Furthermore, in a case where a particle trapping device of the present technology described later is for singly trapping a micro-order microparticle, a fine corrugated structure or a fine first recess has to be formed on the substrate, and the range described above is allowable also from the standpoint of ease of manufacture in such a case.

Additionally, pitches on the left and right of the ridge portion 17 may be the same or different from each other.

Furthermore, if the corrugated structure 20 is formed on the lower surface of the first channel 11 where the lower surface and an upper surface are parallel to each other, a channel width of the first channel 11 may be made relatively small at the ridge portion 17 and relatively great at the trough portion 18. Such a channel width enables the central laminar flow of the liquid flow to be increased, and thus, particles stacked up at the crest portion 19 may be caused to flow.

Figure 5:
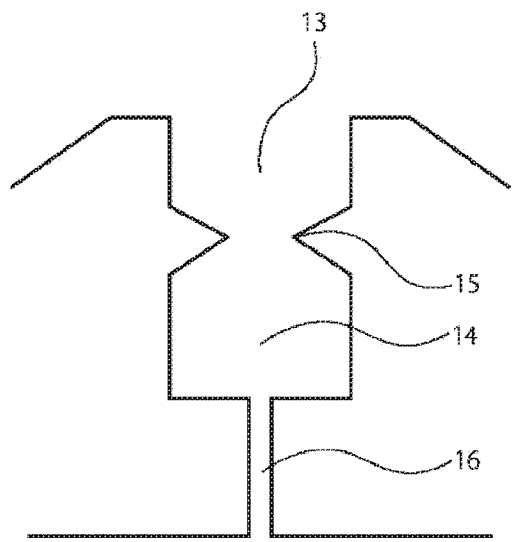
FIG. 5 is a schematic view showing an example of a connecting portion.

A width of the connecting portion 15 is desirably formed narrower than the first recess 13 and the second recess 14 so as to prevent a particle that is trapped in the first recess 13 from flowing out to the second recess 14. The connecting portion 15 shown in FIGS. 1 and 2 has a predetermined length in a vertical direction, but a shape of the connecting portion 15 is not limited to such. FIG. 5 is a schematic view showing an example of the connecting portion 15. As shown in FIG. 5, the connecting portion 15 may be constricted without including a length.

Figure 6:
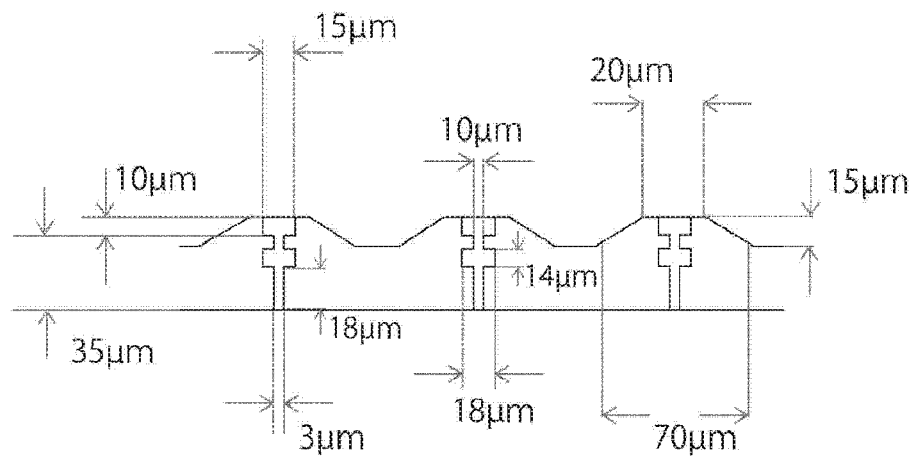
FIG. 6 is a diagram showing an example of a size of each part of the particle trapping chip.

Next, an example of a size of each part will be described with reference to FIG. 6. FIG. 6 is a diagram showing an example of a size of each part of the particle trapping chip 1. The particle trapping chip 1 here is assumed to trap a particle with a diameter of 10 μm. In FIG. 6, a width of the ridge portion 17 is 70 μm, a height of the ridge portion 17 is 15 μm, and a width of the crest portion 19 is 20 μm. Furthermore, a diameter of the opening of the first recess 13 is 15 μm, the depth of the first recess 13 is 10 μm, the width of the connecting portion 15 is 10 μm, a width of the second recess 14 is 18 μm, a height of the second recess 14 is 14 μm, a length of the communicating portion 16 is 18 μm, and a width of the communicating portion 16 is 3 μm.

Figure 7:
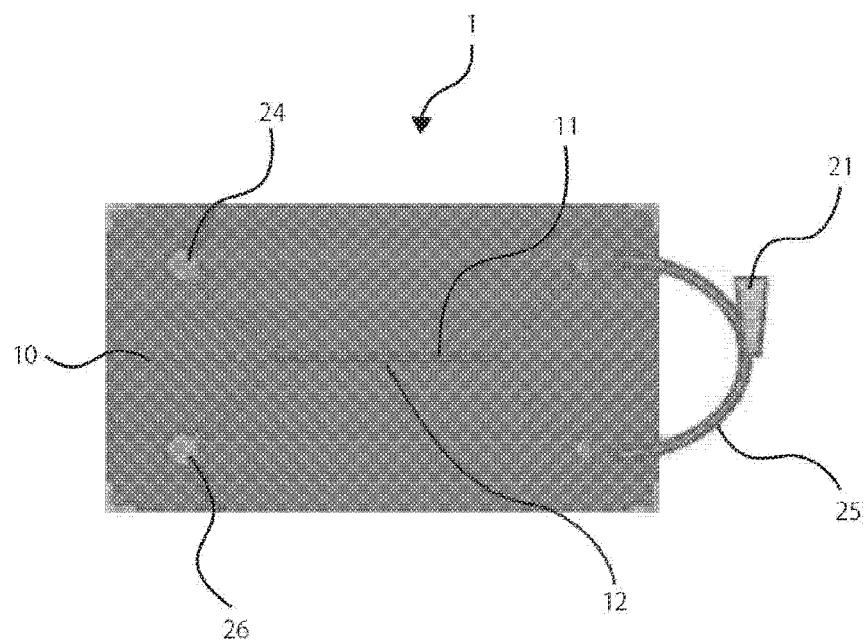
FIG. 7 is a schematic view showing an example of the particle trapping chip.

Next, an example of the particle trapping chip 1 of the present technology will be described with reference to FIG. 7. FIG. 7 is a schematic view showing an example of the particle trapping chip 1. A polydimethylsiloxane (PDMS) resin is molded with PDMS as a material and by placing the material in a mold as a master, and the substrate 10 including the channels, the recesses, the communicating portion and the like described above is fabricated. A surface of the fabricated substrate 10 is hydrophilized by application of direct plasma (DP) asking for 30 seconds under conditions of $O_2$:10 cc and 100 W, and then, a cover glass is stuck in atmosphere, and the particle trapping chip 1 is thereby fabricated.

With the particle trapping chip 1 shown in FIG. 7, the first channel 11 and the second channel 12 are formed at a center portion of the substrate 10. The first recess, the connecting portion, the second recess, and the communicating portion (which are not shown) are formed between the first channel 11 and the second channel 12. A port 24 located at a top left of the substrate 10 is joined to the first channel 11, and a particle-containing sample is introduced to the port 24. A bypass 25 is provided on a right side of the substrate 10, and the bypass 25 connects the first channel 11 and the second channel 12. A valve 21 is provided at the bypass 25. A port 26 located on a bottom left of the substrate 10 is a part where a sample which flowed through the first channel 11 and the second channel 12 is to flow in.

The particle-containing sample introduced from the top left port 24 may flow inside the first channel 11 and the second channel 12 by any or a combination of a force of introducing the particle-containing sample at the first channel 11, a force of downstream flow, a force of flow of the sample caused by opening/closing of the valve 21 provided at the bypass 25, a force of sucking the sample from the bottom left port 26, and the like.

Figure 8:
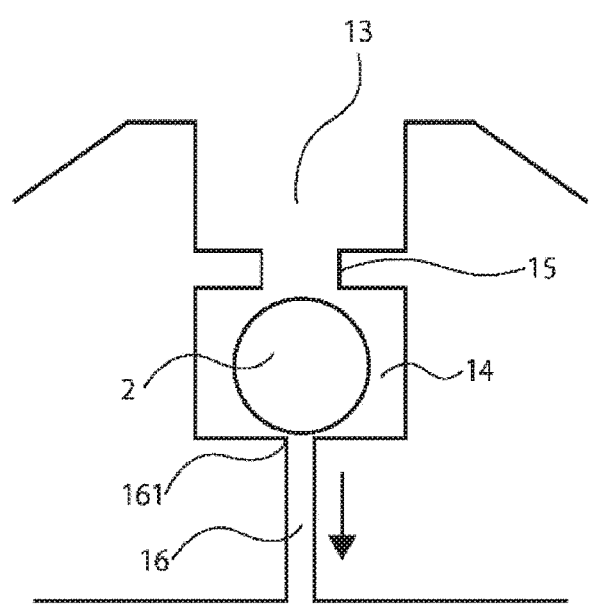
FIG. 8 is a schematic view showing a transverse cross-section of a part of the particle trapping chip.

Next, the particle trapping chip 1 of the present technology will be further described with reference to FIG. 8. FIG. 8 is a schematic view showing a transverse cross-section of a part of the particle trapping chip 1. As shown in FIG. 8, the particle trapping chip 1 desirably includes a plug member 2 that is housed in the second recess 14.

When a sample containing particles is caused to flow, as shown in FIG. 3 described above, a suction force in a downward arrow direction is generated in the communicating portion 16 shown in FIG. 8, but because a suction pressure may be alleviated by the plug member 2, a suction force that is applied to the first recess 11 is reduced.

In a case of a structure where a slit is provided at a well where a cell is to enter, as in the case of the technology described in Patent Document 1 described above, there are cases where it is difficult to appropriately maintain a cell inside the well, due to the cell being greatly deformed by a suction force through the slit, and the cell receiving great stress or being drawn into the slit as a result. If the suction force is reduced, deformation of the cell may be prevented, but then, there are cases where the cell does not reach a wall surface where the well is arranged, or where the cell is not sucked into the well even if the wall surface is reached. The present inventors considered finely adjusting the suction force mechanically or manually, but tuning is difficult, and also, a trapped particle is possibly drawn into the slit by fluctuation of a suction pressure caused at the time of tuning.

The present inventors have extensively conducted studies focusing on the suction force, and have found that a drastic increase in the suction force inside the first recess 11 may be suppressed by providing the second recess 12 between the first recess 11 and the communicating portion 16 and arranging the plug member 2 inside the second recess. Application of an excessive suction pressure on the particle trapped in the first recess 11 may thereby be prevented, and the particle may be prevented from being greatly deformed. Furthermore, the plug member 2 serves to block the trapped particle from flowing down the first recess 11, and the trapped particle may thus be kept in the first recess 11.

That is, the particle trapping chip of the present technology provided with the second recess which is capable of housing the plug member has a structure which is capable of preventing deformation and flowing out of a trapped particle.

Furthermore, in an analysis of a cell, a cell is sometimes desired to be collected without being subjected to unnecessary stress, and the particle trapping chip of the present technology is capable of reducing the suction force that is applied to the cell and of reducing the stress that is exerted to the cell, and is therefore suitable for trapping of cells.

To prevent a particle that is trapped in the first recess 13 from passing through the connecting portion 15 and flowing to the second recess 14, the plug member 2 desirably has a size that covers the connecting portion 15 inside the second recess 14. Furthermore, to more effectively reduce the suction force that is generated in the communicating portion 16, the plug member 2 desirably has a size that covers the communicating portion 16 inside the second recess 14.

In the example shown in FIG. 8, from the standpoint of efficiently generating the suction force at the first recess 13 and the second recess 14, a joining portion 161 between the second recess 14 and the communicating portion 16 is provided below the second recess 14. However, a position of the joining portion 161 is not limited to such a position.

For example, the joining portion 161 between the second recess 14 and the communicating portion 16 may be provided on a side of the second recess 14. FIG. 9 is a schematic view showing an example of the communicating portion 16. In the example shown in FIG. 9, two communicating portions 16 are provided for one second recess 14, and the joining portions 161, 161 of the second recess 14 and the communicating portions 16, 16 are provided on different sides of the second recess 14. A suction force may be generated in a direction indicated by an arrow in FIG. 9 at each of the communicating portions 16, 16. By providing the joining portions 161, 161 on both sides of the second recess 14, even if the plug member 2 is sucked toward the communicating portion 16 on one side by a suction force and the joining portion 161 on the one side is blocked, the joining portion 161 on the opposite side may be maintained in an open state. A drastic reduction in the suction force may thereby be prevented.

Furthermore, the configurations shown in FIGS. 8 and 9 may be combined, and the joining portion 161 may be provided on the lower surface and on both sides of the second recess 14.

Next, an example of a method of housing the plug member 2 in the second recess 14 will be described with reference to FIGS. 10A, 10B, and 10C. FIGS. 10A, 10B, and 10C are diagrams showing an example of a procedure of housing the plug member 2 in the second recess 14. FIG. 10A shows a state where a sample containing the plug member 2 is fed to the first channel 11 in a manner shown in FIG. 3, for example, and where the plug member 2 is trapped in the first recess 13. The suction force is generated in a downward arrow direction in the drawing. Next, the suction pressure is increased, and the plug member 2 is sucked toward the second recess 14 side. FIG. 10B shows deformation of the plug member 2 by high suction pressure, and movement of the plug member 2 from the first recess 13 to the second recess 14 through the connecting portion 15. FIG. 10C shows a state after movement of the plug member 2 to the second recess 14 by the suction force. The plug member 2 may be housed in the second recess 14 by such a procedure.

Next, another example of the method of housing the plug member 2 in the second recess 14 will be described with reference to FIGS. 11A, 11B, and 11C. FIGS. 11A, 11B, and 11C are diagrams showing an example of a procedure of housing the plug member 2 in the second recess 14. FIG. 11A shows a state where a sample containing the plug member 2 is fed to the second channel 12, and where the plug member 2 is being drawn into the communicating portion 16 by a suction force that is generated in an upward arrow direction. In this manner, in FIG. 11A, a suction force in an opposite direction from that in FIGS. 10A, 10B, and 10C are generated. Next, the suction pressure is increased, and the plug member 2 that is trapped in the communicating portion 16 is sucked toward the second recess 14 side. FIG. 11B shows deformation of the plug member 2 by high suction pressure, and movement of the plug member 2 from the communicating portion 16 to the second recess 14. FIG. 11C shows a state after movement of the plug member 2 to the second recess 14 by the suction force. The plug member 2 may be housed in the second recess 14 by such a procedure.

For example, as another method of housing the plug member in the second recess, arranging the plug member in a manufacturing process of the particle trapping chip may be cited. Specifically, the plug member may be housed in the second recess by forming the second recess on the substrate, and then, arranging the plug member inside the second recess, and then, sticking a cover glass on the substrate.

As the plug member, a bead (microbead), which is generally used in sorting and analyzing a microparticle, is desirably used from the standpoint of availability.

A material of the plug member is not particularly limited, but, in a case where the plug member is to be housed in the second recess by a suction force through the communicating portion, as shown in FIGS. 10A, 10B, 11A, and 11B, for example, the material is desirably an elastic material that can be deformed by the suction force.

Furthermore, in the case of FIGS. 10A, 10B, and 10C, the connecting portion desirably includes an elastic member to reduce a load that is generated at the time of the plug member passing through the connecting portion. In the case of FIGS. 11A, 11B, and 11C, the communicating portion desirably includes an elastic member to reduce a load that is generated at the time of the plug member passing through the communicating portion. It is possible to form only the connecting portion or only the communicating portion from an elastic member, but from the standpoint of labor and cost of manufacturing, the substrate itself desirably includes a material having elasticity.

A shape of the plug member is not particularly limited, but a spherical shape is desirable so that a suction pressure that is applied to the plug member in a case of housing the plug member in the second recess by a suction force is not biased.

The number of plug members is not particularly limited, but one plug member is desirably housed in one second recess. If two or more plug members are housed in one second recess, a suction pressure for drawing a particle that is a target of trapping into the first recess has to be increased than in a case where one plug member is housed. That is, if the number of plug members housed in the second recess is one, the suction pressure may be more suppressed, and a load that is applied to the particle trapping chip may thereby be reduced.

Furthermore, the particle trapping chip of the present technology may be used to acquire a substance that is derived from a particle of secretion, contents or the like. For example, a description will be given of a configuration for acquiring a target substance that is derived from a cell, which is a particle that is a target of trapping, by using a plug member on which a binding substance that binds to the target substance is immobilized.

Figure 12:
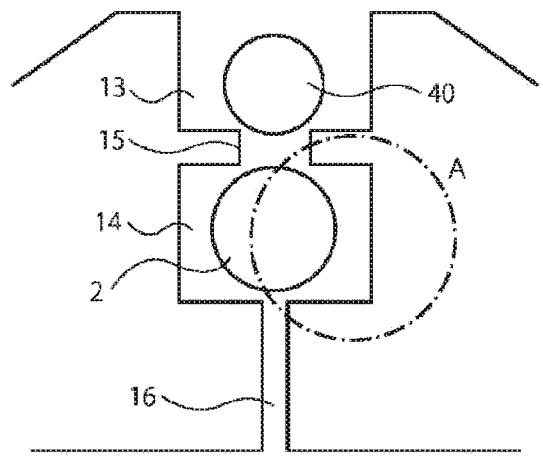
FIG. 12 is a schematic view showing a transverse cross-section of a part of the particle supplementing chip where a particle is trapped.

FIG. 12 is a schematic view showing a transverse cross-section of a part of the particle supplementing chip where a particle is trapped. As shown in FIG. 12, a cell 40 is trapped in the first recess 13. A binding substance (not shown) that binds to a target substance is immobilized on a surface of the plug member 2 shown in FIG. 12.

For example, the target substance may be a cell-derived substance such as nucleic acid, protein, peptide, sugar chain or the like. In a case where the target substance is nucleic acid, an antibody for the nucleic acid, a nucleic acid probe that hybridizes to the nucleic acid, protein that binds to the nucleic acid or the like may be used as the binding substance. In a case where the target substance is protein or peptide, an antibody for the protein, an antibody for the peptide or the like may be used as the binding substance. In a case where the target substance is a sugar chain, an antibody for the sugar chain, lectin for the sugar chain or the like may be used as the binding substance. A method of immobilizing the binding substance on the plug member is not particularly limited, and a known method may be used.

Figure 13:
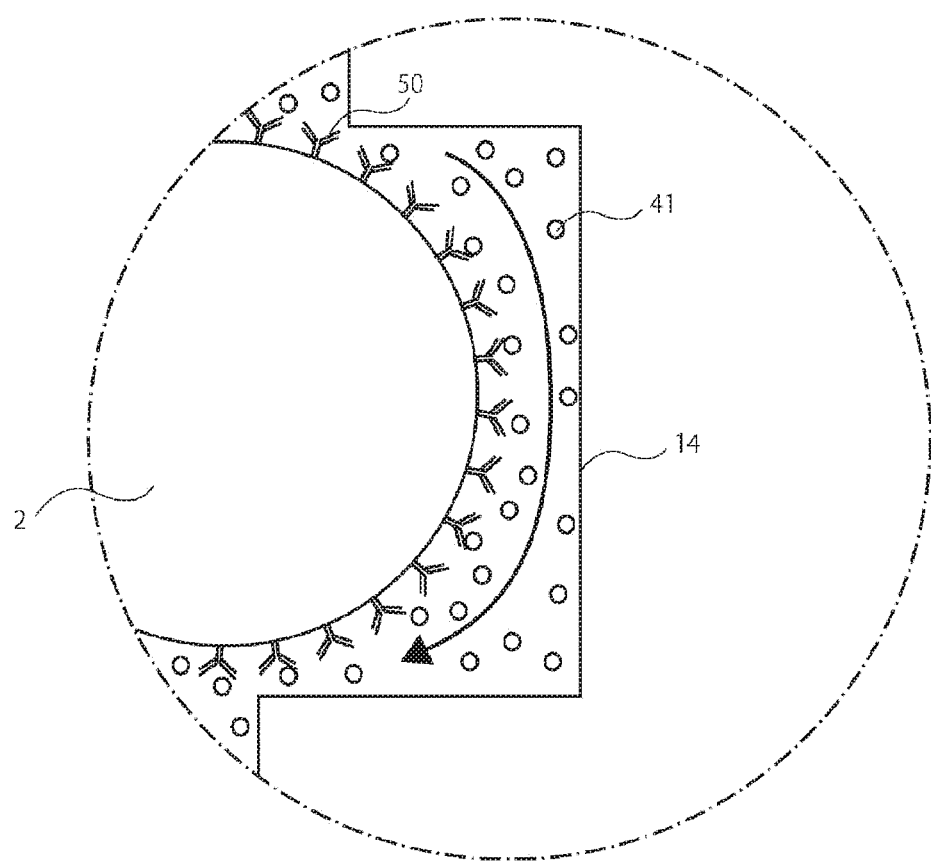
FIG. 13 is an enlarged view of apart surrounded by a dash-dotted line A in FIG. 12.

Next, an example of a case where the binding substance is immobilized on the surface of the plug member 2 will be further described with reference to FIG. 13. FIG. 13 is an enlarged view of a part surrounded by a dash-dotted line A in FIG. 12. Inside the second recess 14, a suction force in an arrow direction in the drawing is generated, and secretion 41 secreted from a cell (not shown) that is trapped in the first recess 13 flows into the second recess 14 from the first recess 13, and moves inside the second recess 14 in the arrow direction. A binding substance 50 that binds to the secretion 41 is immobilized on the surface of the plug substance 2, and the secretion 41 flowing inside the second recess 14 binds to the binding substance 50. Then, the secretion 41 bound to the binding substance 50 may be acquired by collecting the plug substance 2.

Furthermore, a cell that is trapped may be crushed inside the first recess to cause a target substance such as nucleic acid to be released, and the target substance and the binding substance on the plug member may be bound to each other, for example. The target substance bound to the binding substance on the plug member may be acquired by collecting the plug member.

Figure 14:
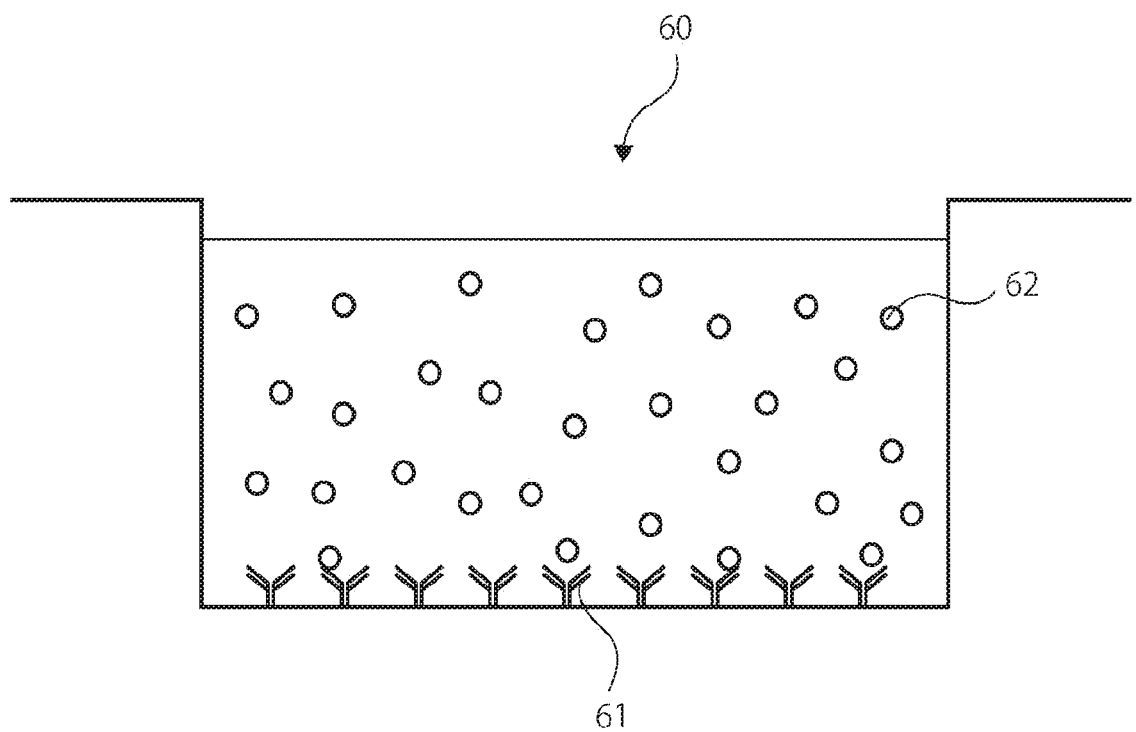
FIG. 14 is a schematic view showing a conventional method for acquiring a cell-derived target substance.

FIG. 14 is a schematic view showing a conventional method for acquiring a cell-derived target substance. As shown in FIG. 14, conventionally, a method of immobilizing a binding substance 61 on a bottom surface of a well 60, and causing a target substance 62 floating inside the well 60 to bind to the binding substance 61 was generally used. On the other hand, as shown in FIG. 13 described above, with the particle trapping chip of the present technology, the target substance flows through a narrow area between the plug member 2 and the second recess 14, and thus, an efficiency of binding between the target substance and the binding substance is increased than with the conventional method. Accordingly, the target substance may be more efficiently acquired than with the conventional method.

Furthermore, by including the first recess and the second recess, the particle trapping chip of the present technology may be applied to a technology of vertically stacking single particles. For example, by providing a large number of first recesses and second recesses, and by housing IC chips in the first recesses and LEDs in the second recesses, a large number of vertically aligned IC chips and LEDs may be acquired at once.

2. Particle Trapping Device

Figure 15:
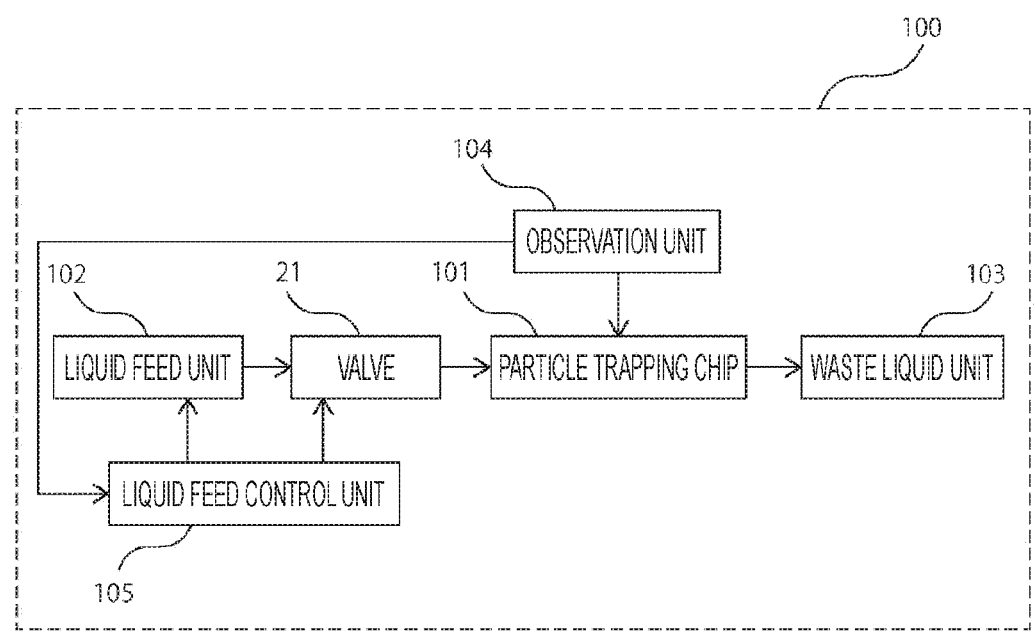
FIG. 15 is a schematic view showing an example of a particle trapping device.

A particle trapping device as another embodiment according to the present technology will be described with reference to FIG. 15. FIG. 15 is a schematic view showing an example of a particle trapping device 100. The particle trapping device 100 includes a particle trapping chip 101 of the present technology described above. The particle trapping chip 101 is connected to a liquid feed unit 102 via the valve 21. The liquid feed unit 102 supplies a particle-containing sample to the particle trapping chip 101. Flow of the sample may be controlled by opening/closing the valve 21. Such control may be performed by a liquid feed control unit 105. By controlling liquid feeding, a sample may be caused to flow or to be stopped, and moreover, backflow and pulsation flow of changing the flow at specific intervals may also be performed.

Furthermore, the particle supplementing device 100 may also include an observation unit 104. Although not particularly limited, with the observation unit 104, flowing and trapping of a particle may be magnified by a microscope or the like to be observed with naked eye, or processing by an image processing device or the like may be enabled so as not to use naked eye. An observation result at this time may be fed back to the liquid feed control unit 105 to further control the flow of the sample.

The particle trapping device 100 may further include a waste liquid unit 103 on a downstream side, and may collect a sample with reduced particle content as a waste liquid. A valve or a pump may be further included on an upstream side or a downstream side of the waste liquid unit 103 to cause a suction force to act on a channel on the particle trapping chip 101.

3. Particle Trapping Method

Figure 16:
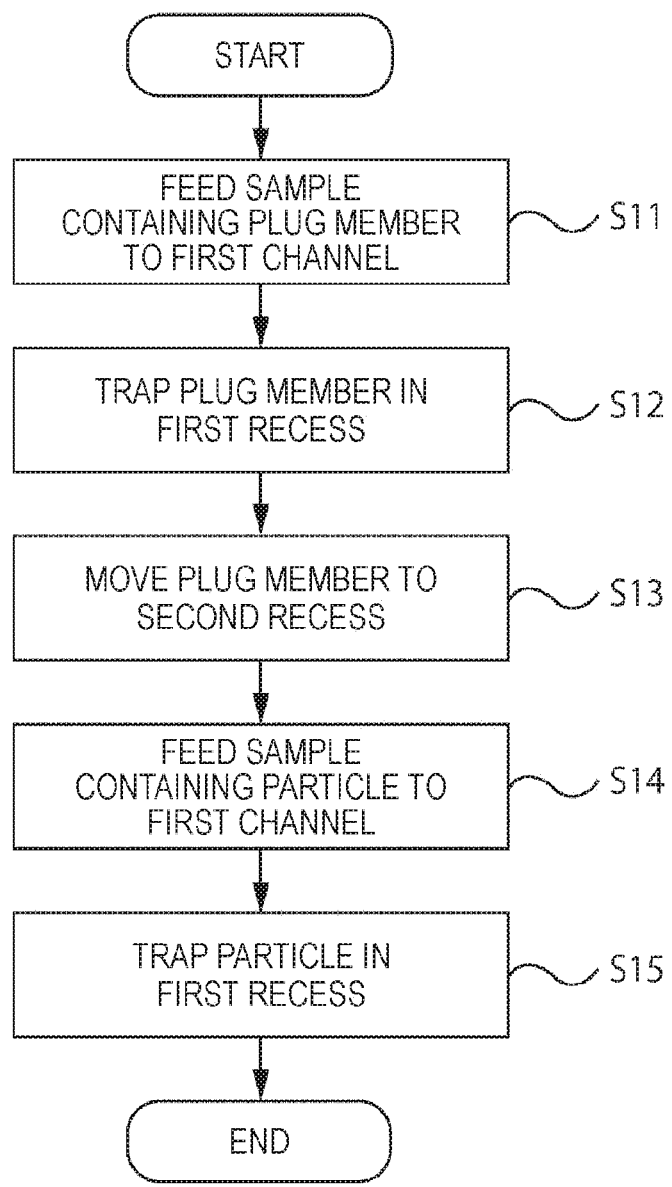
FIG. 16 is a flowchart showing an example of a particle trapping method.

A particle trapping method as another embodiment according to the present technology will be described with reference to FIG. 16. FIG. 16 is a flowchart showing an example of a particle trapping method of the present technology. The particle trapping method shown in FIG. 16 uses a particle trapping chip which does not include the plug member in the second recess.

First, a sample containing the plug member is fed to the first channel (step S11), and the plug member is trapped in the first recess (step S12). Next, the plug member is moved to the second recess by a suction force through the communicating portion (step S13). Then, a sample containing a particle that is a target of trapping is fed to the first channel (step S14), and the particle is trapped in the first recess (step S15).

In a case where the particle is to be trapped by using a particle trapping chip including the plug member in the second recess, it is sufficient if steps S14 and S15 shown in FIG. 16 are performed.

With the particle trapping method of the present technology, liquid may be caused to flow backward. By repeating forward flow and backward flow, particles accumulated on the lower surface of the first channel may be scattered, thereby allowing a greater number of particles to be trapped.

4. Acquisition Method of Target Substance

Figure 17:
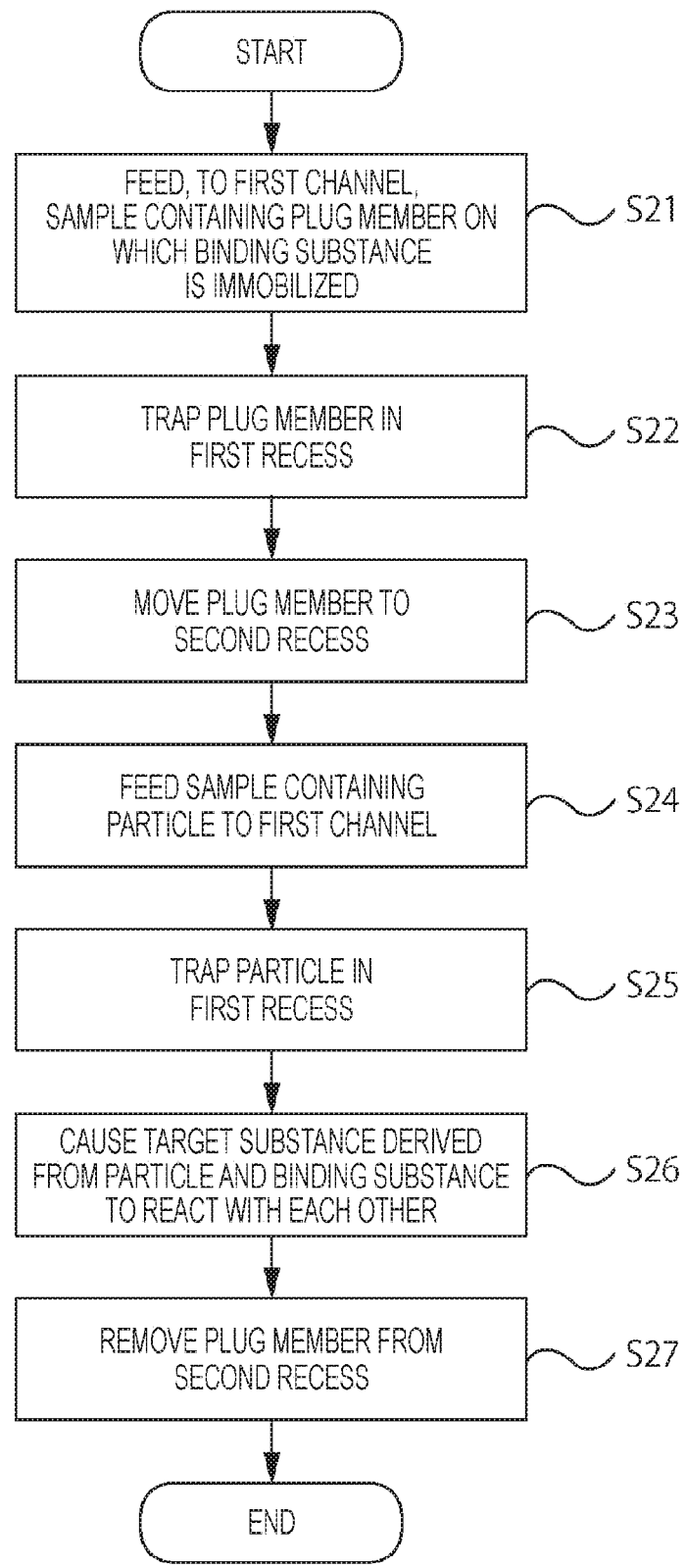
FIG. 17 is a flowchart showing an example of an acquisition method of a target substance.

An acquisition method of a target substance as another embodiment of the present technology will be described with reference to FIG. 17. FIG. 17 is a flowchart showing an example of an acquisition method of a target substance according to the present technology. With the acquisition method of a target substance shown in FIG. 17, a particle trapping chip not including the plug member in the second recess is used.

First, a sample containing a plug member on which a binding substance that binds to a target substance is immobilized is fed to the first channel (step S21), and the plug member is trapped in the first recess (step S22). Next, the plug member is moved to the second recess by a suction force through the communicating portion (step S23). Then, a sample containing a particle that is a target of trapping is fed to the first channel (step S24), and the particle is trapped in the first recess (step S25). The target substance derived from the trapped particle and the binding substance immobilized on the surface of the plug member are caused to react with each other (step S26). By removing the plug member from the second recess, the target substance bound to the binding substance on the plug member is acquired (step S27).

In a case where the target substance is to be acquired by using a particle trapping chip including the plug member in the second recess, it is sufficient if steps S24 to S27 shown in FIG. 17 are performed.

In the acquisition method of a target substance according to the present technology, the method of removing the plug member from the second recess is not particularly limited. For example, the plug member may be removed by using a capillary. Moreover, a liquid flow in an opposite direction from the direction of suction through the communicating portion may be generated, and the plug member may be caused to flow out of the second recess into the first channel by a pressure of such a liquid flow, and then, the plug member may be removed from a plug member-containing liquid by collecting the plug member-containing liquid from the first channel.

Additionally, the present technology may also adopt the following configurations.

(1) A particle trapping chip including:
a first channel;
a second channel;
a first recess that is open on the first channel side;
a second recess that is provided side by side with the first recess;
a connecting portion connecting the first recess and the second recess; and
a communicating portion allowing the second recess and the second channel to communicate with each other.

(2) The particle trapping chip according to (1), further including a plug member that is housed in the second recess.

(3) The particle trapping chip according to (2), in which the plug member includes a bead.

(4) The particle trapping chip according to (2) or (3), in which a binding substance that binds to a target substance is immobilized on a surface of the plug member.

(5) The particle trapping chip according to any one of (1) to (4), in which the connecting portion includes an elastic member.

(6) The particle trapping chip according to any one of (1) to (5), in which a joining portion between the second recess and the communicating portion is provided below the second recess.

(7) The particle trapping chip according to any one of (1) to (6), in which a joining portion between the second recess and the communicating portion is provided on a side of the second recess.

(8) The particle trapping chip according to any one of (1) to (7), in which a lower surface of the first channel includes a corrugated structure including a ridge portion and the trough portion, and the first recess is provided at a crest portion of the ridge portion.

(9) A particle trapping device including:
a particle supplementing chip including
a first channel,
a second channel,
a first recess that is open on the first channel side,
a second recess that is provided side by side with the first recess,
a connecting portion connecting the first recess and the second recess, and
a communicating portion allowing the second recess and the second channel to communicate with each other; and
a liquid feed unit.

(10) The particle trapping device according to (9), further including a waste liquid unit.

(11) The particle trapping device according to (9) or (10), further including an observation unit configured to observe the first recess.

(12) The particle trapping device according to any one of (9) to (11), further including a liquid feed control unit configured to control the liquid feed unit.

(13) A particle trapping method performed using a particle supplementing chip including
a first channel,
a second channel,
a first recess that is open on the first channel side,
a second recess that is provided side by side with the first recess,
a connecting portion connecting the first recess and the second recess, and
a communicating portion allowing the second recess and the second channel to communicate with each other,
the method including:
feeding a sample containing a plug member to the first channel;
trapping the plug member in the first recess;
moving the trapped plug member to the second recess by suction through the communicating portion;
feeding a sample containing a particle to the first channel; and
trapping the particle in the first recess.

(14) The particle trapping method according to (13), further including causing the feeding to be performed backward.

(15) A particle trapping method performed using a particle supplementing chip including
a first channel,
a second channel,
a first recess that is open on the first channel side,
a second recess that is provided side by side with the first recess,
a connecting portion connecting the first recess and the second recess,
a communicating portion allowing the second recess and the second channel to communicate with each other, and
a plug member that is housed in the second recess,
the method including:
feeding a sample containing a particle to the first channel; and
trapping the particle in the first recess.

(16) The particle trapping method according to (15), further including causing the feeding to be performed backward.

(17) An acquisition method of a target substance performed using a particle supplementing chip including
a first channel,
a second channel,
a first recess that is open on the first channel side,
a second recess that is provided side by side with the first recess,
a connecting portion connecting the first recess and the second recess, and
a communicating portion allowing the second recess and the second channel to communicate with each other,
the method including:
a step of feeding, to the first channel, a sample containing a plug member on which a binding substance that binds to the target substance is immobilized, trapping the plug member in the first recess, moving the trapped plug member to the second recess by suction through the communicating portion, feeding a sample containing a particle to the first channel, and trapping the particle in the first recess;

a step of causing the target substance derived from the particle and the binding substance to react with each other; and a step of removing the plug member from the second recess.

(18) The acquisition method of a target substance according to (17), in which the plug member is removed from the second recess by using a capillary.

(19) The acquisition method of a target substance according to (17), in which the plug member is caused to flow out of the second recess into the first channel by generating a liquid flow in an opposite direction from the suction, a plug member-containing liquid is collected from the first channel, and the plug member is removed from the plug member-containing liquid.

(20) An acquisition method of a target substance performed using a particle supplementing chip including
a first channel,
a second channel,
a first recess that is open on the first channel side,
a second recess that is provided side by side with the first recess,
a connecting portion connecting the first recess and the second recess,
a communicating portion allowing the second recess and the second channel to communicate with each other, and
a plug member that is housed in the second recess, and on which a binding substance that binds to the target substance is immobilized,
the method including:
a step of feeding a sample containing a particle to the first channel, and trapping the particle in the first recess;
a step of causing the target substance derived from the particle and the binding substance to react with each other; and
a step of removing the plug member from the second recess.

REFERENCE SIGNS LIST 1, 101 Particle trapping chip
10 Substrate
11 First channel
12 Second channel
13 First recess
14 Second recess
15 Connecting portion
16 Communicating portion
17 Ridge portion
18 Trough portion
19 Crest portion
20 Corrugated structure
21 Valve
22 Flow direction
23 Suction force
24, 26 Port
25 Bypass
30 Particle
40 Cell
41 Secretion
50 Binding substance
100 Particle trapping device
102 Liquid feed unit
103 Waste liquid unit
104 Observation unit
105 Liquid feed control unit
161 Joining portion

The invention claimed is:

1. A particle trapping chip comprising:
a first channel;
a second channel;
a first recess for trapping a particle, the first recess being open on a first channel side and having a diameter greater than a diameter of the particle to be trapped in the first recess;
a second recess that is provided side by side with the first recess;
a connecting portion connecting the first recess and the second recess, wherein a width of the connecting portion is less than the diameter of the particle to be trapped in the first recess and less than a diameter of the second recess; and
a communicating portion allowing the second recess and the second channel to communicate with each other, the communicating portion having a width which is less than the diameter of the second recess.

2. The particle trapping chip according to claim 1, further comprising a plug member that is housed in the second recess.

3. The particle trapping chip according to claim 2, wherein the plug member includes a bead.

4. The particle trapping chip according to claim 2, wherein a binding substance that binds to a target substance is immobilized on a surface of the plug member.

5. The particle trapping chip according to claim 1, wherein the connecting portion includes an elastic member.

6. The particle trapping chip according to claim 1, wherein a joining portion between the second recess and the communicating portion is provided below the second recess.

7. The particle trapping chip according to claim 1, wherein a joining portion between the second recess and the communicating portion is provided on a side of the second recess.

8. The particle trapping chip according to claim 1, wherein a lower surface of the first channel includes a corrugated structure including a ridge portion and a trough portion, and the first recess is provided at a crest portion of the ridge portion.

9. A particle trapping device, comprising: a particle trapping chip according to claim 1;
and a liquid feed unit.

10. The particle trapping device according to claim 9, further comprising a waste liquid unit.

11. The particle trapping device according to claim 9, further comprising an observation unit configured to observe the first recess.

12. The particle trapping device according to claim 9, further comprising a liquid feed control unit configured to control the liquid feed unit.

13. A particle trapping method performed using a particle trapping chip according to claim 1, the particle trapping method comprising:
feeding a sample containing a plug member to the first channel;
trapping the plug member in the first recess;
moving the trapped plug member to the second recess by suction through the communicating portion;
feeding a sample containing a particle to the first channel; and
trapping the particle in the first recess.

14. The particle trapping method according to claim 13, further comprising causing the feeding to be performed backward.

15. A particle trapping method performed using a particle trapping chip according to claim 1, and a plug member that is housed in the second recess, the particle trapping method comprising:
feeding a sample containing a particle to the first channel; and
trapping the particle in the first recess.

16. The particle trapping method according to claim 15, further comprising causing the feeding to be performed backward.

17. An acquisition method of a target substance performed using a particle trapping chip according to claim 1, the acquistion method comprising:
a step of feeding, to the first channel, a sample containing a plug member on which a binding substance that binds to the target substance is immobilized, trapping the plug member in the first recess, moving the trapped plug member to the second recess by suction through the communicating portion, feeding a sample containing a particle to the first channel, and trapping the particle in the first recess;
a step of causing the target substance derived from the particle and the binding substance to react with each other; and a step of removing the plug member from the second recess.

18. The acquisition method of a target substance according to claim 17, wherein the plug member is removed from the second recess by using a capillary.

19. The acquisition method of a target substance according to claim 17, wherein the plug member is caused to flow out of the second recess into the first channel by generating a liquid flow in an opposite direction from the suction, a plug member-containing liquid is collected from the first channel, and the plug member is removed from the plug member-containing liquid.

20. An acquisition method of a target substance performed using a particle supplementing chip including:
a first channel,
a second channel,
a first recess that is open on a first channel side,
a second recess that is provided side by side with the first recess,
a connecting portion connecting the first recess and the second recess,
a communicating portion allowing the second recess and the second channel to communicate with each other, and
a plug member that is housed in the second recess, and on which a binding substance that binds to the target substance is immobilized,
the acquistion method comprising:
a step of feeding a sample containing a particle to the first channel, and trapping the particle in the first recess;
a step of causing the target substance derived from the particle and the binding substance to react with each other; and
a step of removing the plug member from the second recess.

* * * * *